US005634926A

United States Patent [19]
Jobe

[11] Patent Number: 5,634,926
[45] Date of Patent: Jun. 3, 1997

[54] SURGICAL BONE FIXATION APPARATUS

[76] Inventor: Richard P. Jobe, 26985 Orchard Hill, Los Altos Hills, Calif. 94022

[21] Appl. No.: 428,913

[22] Filed: Apr. 25, 1995

[51] Int. Cl.⁶ .................................................. A61B 17/56
[52] U.S. Cl. ........................... 606/69; 606/72; 606/75; 606/101
[58] Field of Search .................... 606/69, 70, 71, 606/72, 73, 75, 61, 60, 54, 101

[56] References Cited

U.S. PATENT DOCUMENTS

| | | | |
|---|---|---|---|
| 2,489,870 | 11/1949 | Dzus | 606/73 |
| 4,454,876 | 6/1984 | Mears | 128/92 |
| 4,655,230 | 4/1987 | Törmälä et al. | 128/92 |
| 4,905,680 | 3/1990 | Tunc | 606/69 |
| 4,960,420 | 10/1990 | Goble et al. | 606/72 |
| 4,966,599 | 10/1990 | Pollock | 606/69 |
| 5,037,422 | 8/1991 | Hayhurst et al. | 606/72 |
| 5,053,038 | 10/1991 | Sheehan | 606/75 |
| 5,057,111 | 10/1991 | Park | 606/69 |
| 5,139,497 | 8/1992 | Tilghman et al. | 606/69 |
| 5,180,381 | 1/1993 | Aust et al. | 606/61 |
| 5,201,736 | 4/1993 | Strauss | 606/69 |
| 5,201,737 | 4/1993 | Lebinger et al. | 606/69 |
| 5,246,441 | 9/1993 | Ross et al. | 606/53 |
| 5,275,601 | 1/1994 | Gogolewski et al. | 606/72 |
| 5,290,281 | 3/1994 | Tschakaloff | 606/28 |
| 5,372,598 | 12/1994 | Luhr et al. | 606/69 |
| 5,443,482 | 8/1995 | Stone et al. | 606/232 |

OTHER PUBLICATIONS

Brochure for Suretac Fixation Device, Acufex Microsurgical, Inc., Mansfield, MA, 1991.
Brochure for TAG, Acufex Microsurgical, Inc., Mansfield, MA, 1993.

*Primary Examiner*—Michael Powell Buiz
*Assistant Examiner*—Mark S. Leonardo
*Attorney, Agent, or Firm*—Flehr, Hohbach, Test, Albritton & Herbert

[57] ABSTRACT

A bone fixation apparatus for anchoring a surgical member to bone for the fixation of bone or soft tissue to bone. The bone fixation apparatus includes a post device having a leg portion slidably insertable into a hole formed in bone. The leg portion is of sufficient length relative to the interior diameter of the hole to resist removal of the leg portion from the hole when forces substantially parallel to the outer surface of the bone are applied to the post device to anchor the surgical member to bone. In one aspect of the invention, the surgical member is a plate section of an elongated sheet of surgical plate material which may be divided into a plurality of plate sections each having an arbitrary shape.

27 Claims, 5 Drawing Sheets

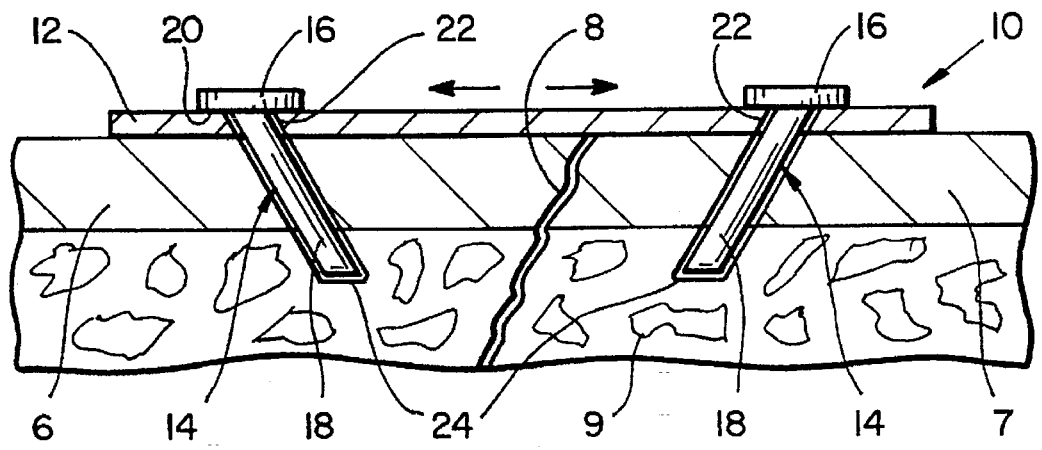
FIG_1
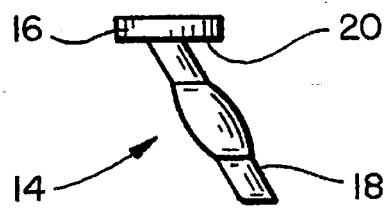
FIG_1A
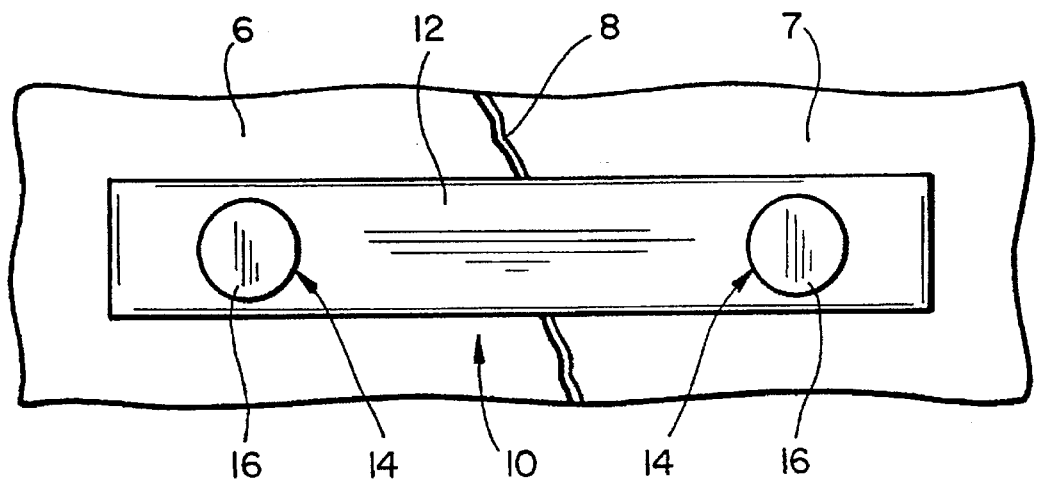
FIG_2

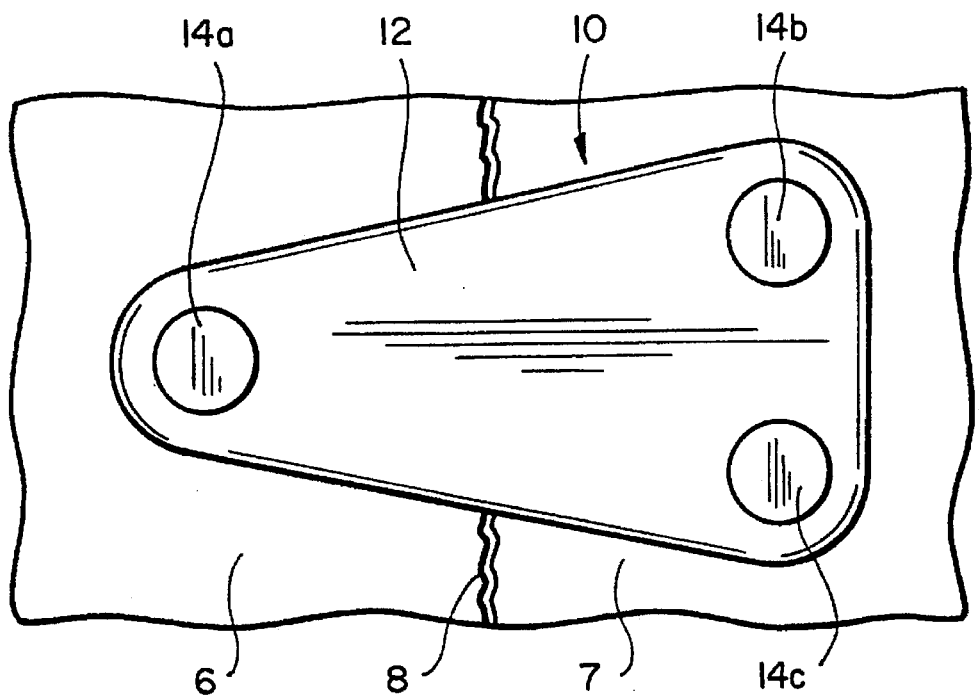
FIG_3
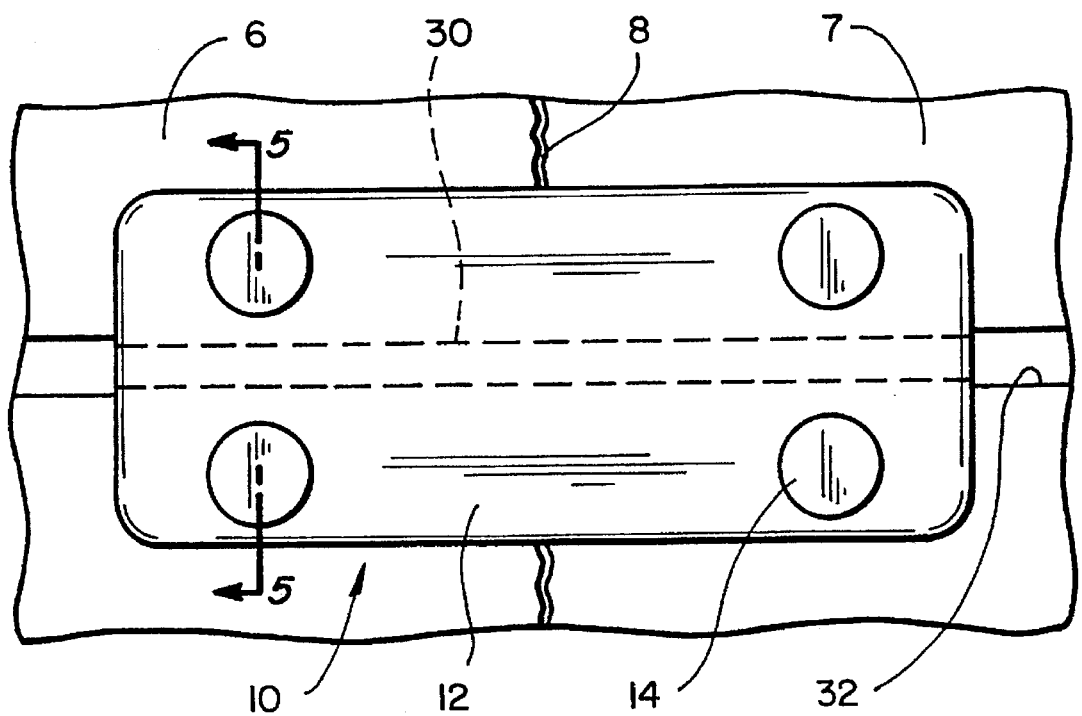
FIG_4

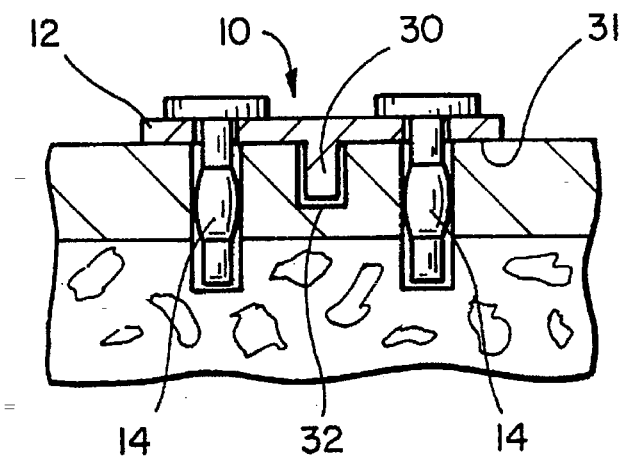
FIG_5
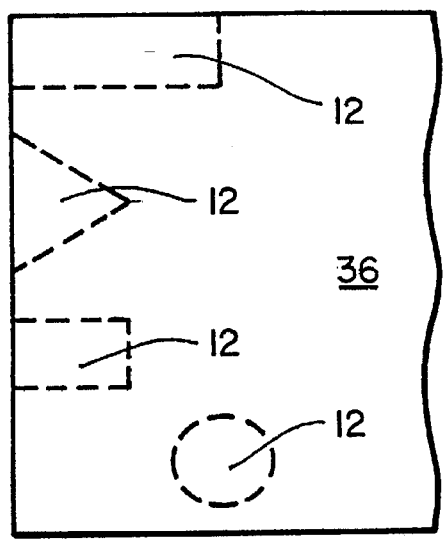
FIG_6
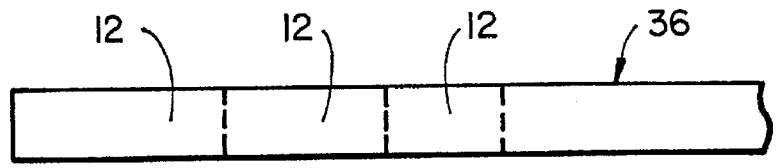
FIG_6A

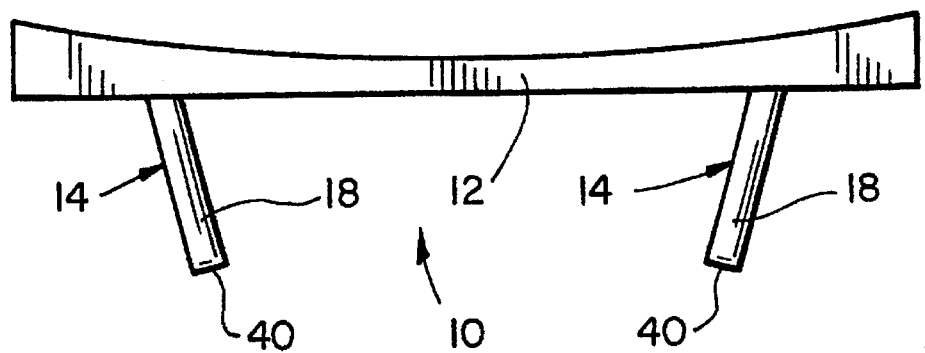
FIG_7
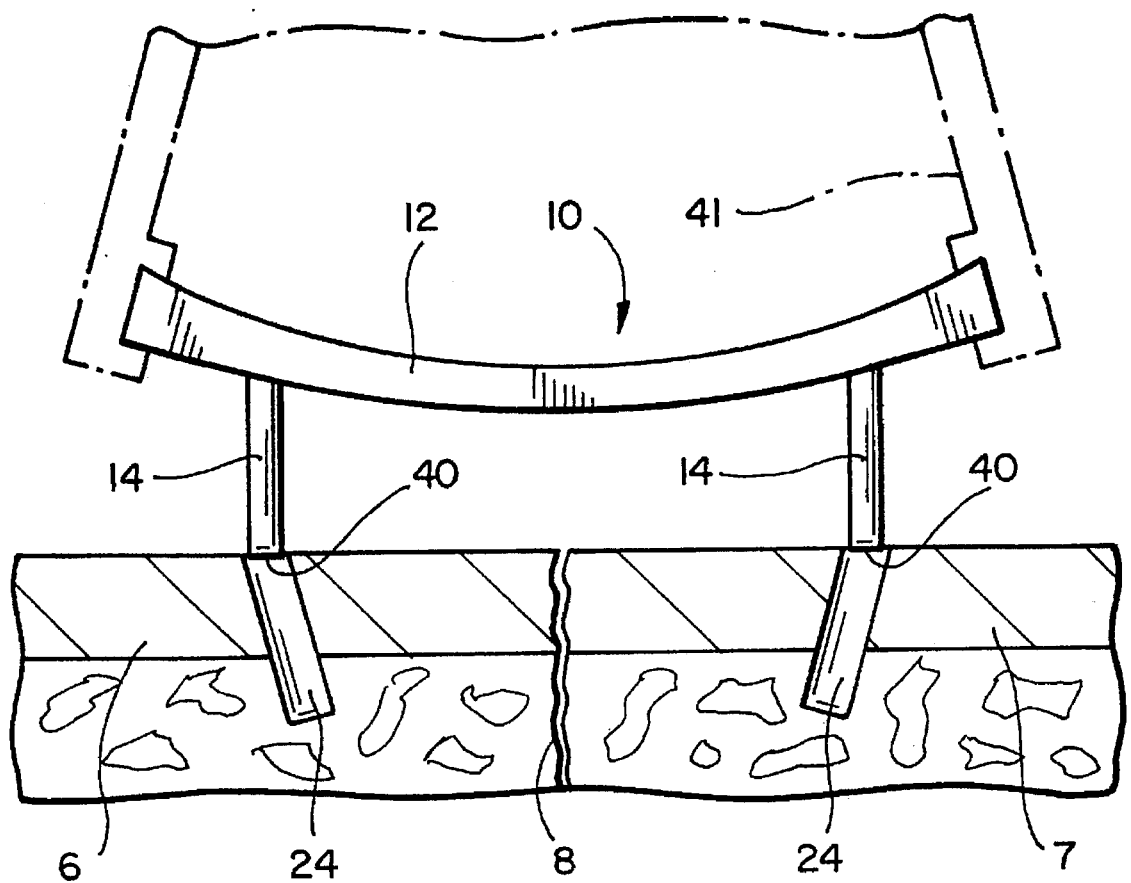
FIG_8

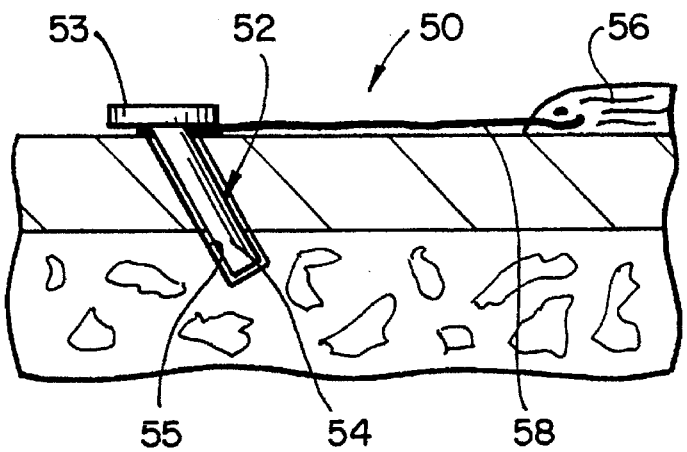
FIG_9
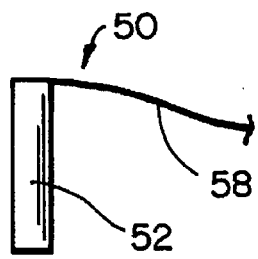
FIG_10
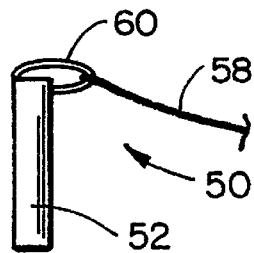
FIG_11
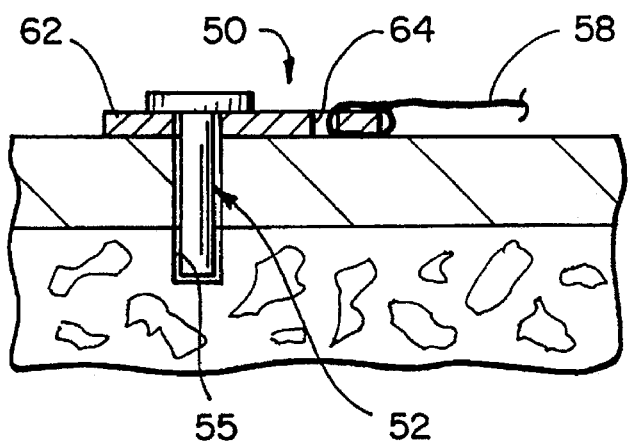
FIG_12

SURGICAL BONE FIXATION APPARATUS

BRIEF DESCRIPTION OF THE INVENTION

This invention relates in general to a surgical bone fixation apparatus and, more particularly, to an apparatus for the fixation of bone and soft tissue to bone.

BACKGROUND OF THE INVENTION

Various surgical plates have been employed in the treatment of traumas to facial or cranial bone structure, plastic surgery, reconstructive facial surgery, and the like to hold the bone sections or fragments in place during the healing process. The surgical plates are positioned against the surface of the bone sections which must be held together and fixed to the bone by mechanical fasteners such as bone screws, wire sutures or other fasteners which secure the plate to the bone surface. The fasteners are securely pressed or embedded in the bone to prevent the surgical plates from being pulled away from the surface of the bone sections. U.S. Pat. Nos. 4,966,599 and 5,290,281 disclose examples of bone stabilization plates which are secured to the bone structure, for example facial or cranial bones, by bone screws. U.S. Pat. No. 4,655,203 discloses a surgical device for immobilization of bone fracture which includes a stiff plate and stiff fixing elements which may be pressed into notches formed in the bone.

In such procedures as rotator cuff surgery and hand tendon surgery, tendons or other soft tissues are fixedly secured to bone. The tendons or other tissue are often secured to bone by feeding the soft tissue through holes formed in the bone and suturing the tissue in place. Another method of securing soft tissue to bone employs a fixation device which essentially tacks the tendon to bone. Unless the tendon or other soft tissue is completely immobilized, the fixation device must be securely embedded in the bone to hold the tendon stationary against the bone surface, resisting those forces tending to pull the tendon away from the bone surface, until the tendon has become attached to the bone. Another method of securing tendons and other soft tissue to bone uses a fixation device with an attached suture. Once again, the fixation device must be securely embedded in bone to resist forces tending to pull the tissue away from the bone surface. In various facial surgery procedures, soft tissue is surgically lifted or moved and then secured to bone by suturing and the like to hold the tissue in the desired position during the healing process. These tissues are generally subjected only to gravitational forces or other forces parallel to the surface of the bone, they are not exposed to forces tending to pull the tissue outwardly away from the bone.

Surgical plates must be securely affixed to bones which may be exposed to various tensile and bending forces during the healing process to prevent the plate from being pulled outwardly away from the bone. If the fasteners do not securely engage the bone, the applied stresses may have a tendency to pull the fasteners from the bone. Facial and cranial bone sections, on the other hand, are generally not exposed to such tensile and bending stresses. Instead, the bone sections are primarily subjected to forces tending to spread the bone sections apart or to cause lateral slippage of the bone sections along the fracture line. Since the applied forces are substantially parallel to the bone surface, the fasteners need only anchor the surgical plates to the facial or cranial bones to hold the bone sections in place. The additional security provided by securely embedding the fastener in bone and actually securing the plate to the bone surface is often not required with facial and cranial bones and of bones at other sites.

Securely embedding screws, nails and the like in bone is a time consuming and labor intensive process, considerably extending the time required to complete the operation. Even when the fasteners are initially inserted into pre-drilled holes, care must be taken to ensure that the desired orientation of the fasteners is maintained. Moreover, embedding the fasteners in bone may subject the relatively fragile facial bones to additional unnecessary stress. Surgical fasteners such as screws and the like require expensive manufacturing techniques because of the small size of the fastener. Minimizing the size of the plate and fastener would minimize the size of the surgical area and the amount of bone which must be exposed. However, the reduced size of the screws and other fasteners is limited because the fasteners have sufficient strength to engage bone and securely attach the plate to the bone. Using a fixation device which anchors the surgical plate to the bone, but does not securely affix the plate to the bone surface, would avoid the disadvantages associated with embedding the fastener in bone. Such a fixation device would also be particularly useful in other types of procedures where the fixation apparatus may be employed to affix soft tissue to bone.

The surgical plates and associated fasteners employed for bone fixation have been fabricated of materials such as titanium, stainless steel, vitalium, chrome cobalt, and suitable bio-compatible polymeric materials. Unless removed by surgery, the plates and fasteners formed of these materials permanently remain in the patient's body. The surgical plates and internal fastening members may cause various unpredictable problems if left intact as the bone dynamically reacts to the foreign bodies over time by molding to the shape of the foreign body, forming deposits on the foreign body, and responding to stress. The foreign bodies also provide potential cites for infection. Migration of the foreign body presents another problem if the surgical plate and/or fasteners are left in the patient's body. This problem is of particular concern when the patient is an infant or young child, where the considerable mount of skull growth has resulted in significant migration of foreign body to the extent where the plate has entered the brain.

Forming the plate and/or fasteners of a material which may be absorbed by the body over time would allow the foreign materials to be removed from the patient's body without requiting a second operation. U.S. Pat. Nos. 5,655,203, 4,905,680, 4,966,599, 5,275,601 and 5,290,281 describe forming the surgical plates and/or fasteners of absorbable materials. Fabricating a bone screw or other mechanical fastener out of absorbable polymers is often difficult because the absorbable fastener has a tendency to prematurely slip from the bone. Moreover, because of their reduced size, forming absorbable bone screws for the fixation of plates to facial and cranial bones is even more difficult. To achieve the desired strength, the absorbable screws must be larger in size than a comparable metal screw. A fixation device for the fixation of surgical plates to bone which may be easily manufactured of an absorbable material and reliably used is highly desirable.

OBJECTS AND SUMMARY OF THE INVENTION

It is a primary object of this invention to provide a bone fixation apparatus for the surgical fixation of bone or soft tissue to bone.

It is another object of this invention to provide a bone fixation apparatus for anchoring a surgical plate, suturing element or other surgical member to bone.

It is yet another object of this invention to provide a bone fixation apparatus which may be quickly and easily applied to bone by the surgeon without subjecting the bone to unnecessary stresses.

It is still another object of this invention to provide a bone fixation apparatus in which the size of the post fixation device may be minimized.

It is a further object of this invention to provide a bone fixation apparatus which may be fabricated of materials which are absorbed by the body over time.

A more general object of this invention is to provide a bone fixation apparatus which may be economically manufactured and which may be efficiently and reliably employed in the fixation of surgical plates, suturing elements and other surgical members to bone.

In summary, this invention provides a bone fixation apparatus which is particularly suitable for use in the fixation of bone and/or soft tissue to bone. In one modification of the invention, the bone fixation apparatus generally includes at least one post device having a leg portion configured for releasable insertion into a hole formed in bone. The leg portion is of sufficient length relative to the interior diameter of the hole to resist removal of the leg portion from the hole in the bone when forces substantially parallel to the outer surface of the bone are applied to the post device. The post device anchors a surgical member, such as a surgical plate or suturing element, to bone. In another modification of the invention, the bone fixation device includes a continuous, elongated sheet of surgical plate material which is divisible into a plurality of plate members each having an arbitrary length. The plate members are mountable to the bone by fastening devices such as the post device.

Additional objects and features of the invention will be more readily apparent from the following detailed description and appended claims when taken in conjunction with the drawings.

BRIEF DESCRIPTION OF THE DRAWINGS

FIG. 1 is an enlarged, fragmentary, cross sectional view of a bone fixation apparatus in accordance with this invention, shown fixed to two bone sections.

FIG. 1A is an enlarged, fragmentary view of a modified post device.

FIG. 2 is an enlarged, fragmentary, top plan view of the bone fixation apparatus and bone sections of FIG. 1.

FIG. 3 is an enlarged, fragmentary, top plan view of a bone fixation apparatus in accordance with another embodiment of the invention.

FIG. 4 is an enlarged, fragmentary, top plan view of a bone fixation apparatus in accordance with yet another embodiment of the invention.

FIG. 5 is a fragmentary, cross sectional view taken along line 5—5 of FIG. 4.

FIGS. 6 and 6A are schematic, top plan views of a bone fixation apparatus in accordance with another embodiment of the invention.

FIG. 7 is an enlarged, side elevational view of a bone fixation apparatus in accordance with another embodiment of the invention.

FIG. 8 is an enlarged, side elevational view of the bone fixation apparatus of FIG. 7, shown during application of the apparatus to the bone sections.

FIGS. 9 is a schematic, fragmentary, side elevational view of a bone fixation apparatus in accordance with another embodiment of the invention, shown securing soft tissue to bone.

FIGS. 10–12 are fragmentary, side elevational views of other modifications of the bone fixation apparatus shown in FIG. 9.

DETAILED DESCRIPTION OF THE INVENTION

Reference will now be made in detail to the preferred embodiment of the invention, which is illustrated in the accompanying figures. Turning now to the drawings, wherein like components are designated by like reference numbers throughout the various figures, attention is directed to FIGS. 1 and 2.

A bone fixation apparatus 10 incorporating this invention may be used for the fixation of bone or soft tissue to bone. In the modification of FIGS. 1 and 2, the bone fixation apparatus 10 is shown holding two bone sections 6 and 7 in a desired position about a fracture line or incision, generally designated 8. Fixation apparatus 10 may be used with any type of bone structure as for example cancellous bones with marrow 9, bones without marrow such as the walls of the sinus, and the skull which includes an outer table, an inner table and marrow between the inner and outer tables. Preferably, the fixation apparatus 10 of the invention is used with bones which are subjected primarily to forces parallel to the bone surface, such as those which tend to separate the bone sections or cause relative lateral movement of the bone sections. The bones are generally isolated from forces transverse to the bone surface and are not required to carry a significant load. Examples of such bones include the facial and cranial bones, although it will be understood that use of the bone fixation apparatus may also be used with other suitable bones.

In the embodiment shown in FIG. 1, bone fixation apparatus 10 includes a surgical plate member 12 extending across the surface of the bone and post devices 14 retaining plate member 12 in place. The shape, size and thickness of plate member 12 is subject to considerable modification depending upon the location of bone sections 6 and 7, the size of fracture line 8, the characteristics of the material of plate member 12, the characteristics and desired result of the surgical procedure employing the apparatus and the like. Surgical plate member 12 is anchored to each bone section by at least one post device 14. In many applications, using one post device 14 per bone section as shown in FIGS. 1 and 2 will sufficiently retain the bone sections in the desired position. However, using more than one post device for at least one of the bone sections offers the advantage of increased stability and augmented parallelographic force. For example, FIG. 3 shows a modification of the invention where one post device 14a anchors plate member 12 to bone section 6 and two post devices 14b and 14c anchor the plate to bone section 7. The positioning of post devices 14a, 14b and 14c creates a triangulation effect which substantially resists relative lateral movement of the bone sections along the fracture line. Instead of using three post devices 14 for enhanced stability as shown in FIG. 3, a greater number of post devices 14 may be employed if desired.

If additional security is desired, plate member 12 may be secured to bone by replacing one of the post devices 14, for example post device 14a shown in FIG. 3, with a screw or other suitable fastener which securely engages the walls of hole 24 to attach the plate member to the surface of the bone section. The remaining post devices, such as post devices 14b and 14c, anchor the plate member 12 to the other bone section to retain the bone sections in the desired position.

As shown in FIG. 1, post device 14 includes an enlarged cap or end portion 16 and a leg portion 18 depending from the underside 20 of end portion 16. The leg portion 18 extends through an aperture 22 formed in plate member 12 and is positioned in a hole 24 formed in bone sections 6 and 7 to anchor surgical plate 12 to the bone sections. Unlike the fixation devices of the prior art, post device 14 is not intended to prevent the surgical plate 12 from being pulled away from the surface of the bone sections. Instead, post device 14 substantially resists forces parallel to the surface of the bone, such as those tending to separate the bone sections or cause lateral slippage along the fracture line, to hold surgical plate 12 in place. Leg portion 18 is formed of sufficient length relative to the interior diameter of the hole 24 to resist those forces parallel to the bone surface. The optimum length for leg portion 18 depends in part on such factors as the stiffness of the material used in the fabrication of post device 14 and the magnitude of the forces applied to the post device. For many applications, a length of at least about two times the interior diameter of the hole 24 will be sufficient to prevent forces parallel to the bone surface from deforming the leg portion and pulling the leg portion 18 from the bone. However, it will be understood that in some applications of the invention it may be desirable to provide leg portion 18 with a lesser or greater length or angle.

Since it is the length of the leg portion 18 which holds the post device 14 in the hole and anchors the plate member 12 to the bone sections, leg portion 18 may be shaped so that only a minimum amount of pressure is required to slip the leg portion into the hole 24. The leg portion 18 is not securely embedded in place, but is instead movable in a direction parallel to the axis of the hole. The exterior of leg portion 18 may be substantially cylindrical as shown in FIG. 1, or, if desired, leg portion 18 may be configured to provide a limited area of engagement between the exterior of the leg portion and the walls of hole 24. For example, FIG. 1A shows a modification of post device 14 having a slightly bowed or spindle-shaped cross section, although it is to be understood that leg portion 18 may have other cross sectional shapes if desired. Moreover, the area of limited engagement need not extend around the entire circumference of the leg portion 18. Instead, leg portion 18 may be formed with one or more projections which are configured to slightly engage the interior wall of hole 24.

The maximum diameter of the spindle-shaped leg portion shown in FIG. 1A is preferably equal to or slightly greater than the interior diameter of the hole 24 so that when the post device 14 is initially inserted in the hole, the leg portion will partially engage the wall of the hole. Although the limited engagement between the leg portion and wall of the bone is generally insufficient to securely retain the post in the hole 24, the spindle shape of leg portion 18 allows the surgeon to conveniently manipulate the surgical plate relative to the bone sections during the surgical procedure without pulling the post device from the hole 24. Since only a limited area of leg portion 18 engages the walls of the bone, the pressure required to insert the post device 14 into hole 24 is not significantly increased.

As is shown particularly in FIG. 1, leg portion 18 is preferably oriented at an angle of about 15 to 55 degrees relative to the underside 20 of the end portion 16. For optimum effectiveness, the angled leg portion 18 is inserted into a hole 24 extending into the bone at approximately the same angle as the inclination of leg portion 18 so that the underside 20 of the end portion engages the upper surface of the plate member 12. Aperture 22 may also extend through plate member 12 at an angle. When post device 14 is inserted in the bone, the angled leg portion 18 is preferably oriented so that the tip of the leg portion points in a direction opposite the forces applied to the bone section. For example, in FIG. 1 the angled leg portion 18 is oriented inwardly toward the fracture line, extending in a direction opposite those forces tending to pull the bone sections 6 and 7 apart.

Providing post device 14 with a slanted leg portion increases the stability of bone fixation apparatus 10 in resisting forces parallel to the bone sections 6 and 7. When positioned as shown in FIG. 1, the slanted leg portions of the post devices 14 on opposite sides of the fracture line may also be used to urge the bone sections 6 and 7 together. Urging the bone sections together with post devices 14 ensures the bone sections are held together, facilitating the healing process. Although angled leg portions 18 increase the ability of post device 14 to resist forces substantially parallel to the bone sections, it will be understood that the leg portions 18 may also be perpendicular to the underside of end portion 16 if desired.

The bone fixation apparatus 10 may be applied to the selected bone sections using a suitable surgical technique. Apertures 22 may be formed in plate member 12 at predetermined locations or, if desired, the surgeon may select the site of the apertures. If desired, the apertures 22 and holes 24 may be formed simultaneously by locating the plate member 12 on the bone sections 6 and 7 and drilling through the plate and bone. However, forming the apertures 22 separately from the holes 24 isolates the wound or surgical site from unwanted surgical plate fragments. The locations of holes 24 may be selected using a template if desired. Preferably, holes 24 are formed using a drill or other appropriate instrument having a stop or collar limiting the hole depth to avoid excess penetration particularly in the skull. When post devices 14 having angled leg portions 18 are employed, the stop is preferably oriented at an angle relative to the drill bit similar to the angle between the end portion 16 and leg portion 18. Alternatively, the stop may be curved for usage with post devices angled or perpendicular to the end portion 16.

The configuration of surgical plate member 12 is subject to considerable variation depending upon the constraints of a particular application. FIG. 2 shows a plate member 12 having a substantially rectangular shape. The plate member may also have other shapes such as the triangular shape shown in FIG. 3. FIGS. 4 and 5 show another embodiment of the invention in which plate member 12 includes a flange or rib 30 depending from the underside 31 of the plate member 12. In the embodiment shown in FIGS. 4 and 5, the flange 30 extends continuously along the entire length of the plate member. However, flange member 30 may have other configurations if desired. Flange 30 is positioned in a thin groove or cut 32 formed in the bone to assist in obtaining the desired positioning of bone fixation apparatus 10 and bone sections 6 and 7 when the apparatus 10 is initially anchored to the bone. The inter-engagement of flange 30 and groove 32 also provides additional resistance against relative lateral slippage between the bone sections 6 and 7. In the modification shown in FIGS. 4 and 5, four post devices 14 having a spindle-shaped cross section are employed to anchor plate member 12 to bone. The post devices 14 may have slanted leg portions or leg portions substantially perpendicular to the plate member 12.

Although not shown, the plate member may also be formed with a curved or stepped cross-section. The curved or stepped configuration may be prefabricated or the plate member may be formed of a suitable material and manipulated into the desired shape by the surgeon or surgical assistant. The prefabricated plate member may also be formed of a material which allows the shape of the plate member to be adjusted during the operation.

FIG. 6 illustrates a modification of the invention in which plate member 12 comprises a section of an elongated sheet 36 of surgical plate material. The sheet 36 shown in FIG. 6 is of sufficient width to allow the surgeon select any shape desired for the surgical plate. Alternatively, as is shown in FIG. 6A the sheet 36 may be formed as a narrow strip of material which may be separated into plate sections of arbitrary lengths. The ability to divide the sheet 36 of plate material into plate sections each having an arbitrary shape provides the surgeon with immediate access to a plate member 12 of appropriate size. The sheet 36 of surgical plate material may be divided into separate plate sections using the appropriate clipping tools for the particular material of sheet 36. Depending upon the material employed for surgical sheet 36, the sheet 36 may be retained in a roll or provided as a planar sheet of material. As with the previously described embodiments, apertures may be pre-formed in sheet 36 or the apertures may be formed by the surgeon at the desired locations. Alternatively, as will be described in greater detail in relation to FIGS. 7 and 8, sheet 36 may be integrally formed with a plurality of spaced post devices 14.

Turning to FIGS. 7 and 8, bone fixation device 10 is a monolithic structure in which post devices 14 are integrally formed with plate member 12. In the modification shown in FIGS. 7 and 8, the leg portions 18 of the post devices 14 are oriented at an angle relative to the underside of plate member 12. The fixation apparatus is applied to bone by deforming the edges of plate member 12 upwardly as shown in FIG. 8 to position the tips 40 of the post device above the open ends of the holes 24. Preferably, the upper surface of the plate 12 is concave to facilitate deformation of the plate to bring the post devices 14 into a substantially parallel orientation. The post devices 14 are then slipped into the holes and the plate member 12 is moved toward the bone surface. The plate member 12 returns to its original shape shown in FIG. 7, with the angled post devices 14 providing addition resistance against separation, when the outer edges of the plate member are released and the plate member is positioned against the bone surface. Preferably, a surgical instrument 41 is used to bend the plate 14 and hold the plate as shown in FIG. 8, allowing a nurse or surgical technician to prepare the plate for insertion and allowing the surgeon to manipulate the plate to the desired position. The surgical instrument may also be used to adjust the position of the fixation apparatus or to remove the fixation apparatus from the bone.

The post devices 14 anchor the fixation apparatus to bone to retain the bone sections in the desired position during healing. As previously described, the angled leg portions 18 provide increased resistance to oppose forces substantially parallel to the bone surface and retain the bone sections in place. In the present embodiment, the post devices are preferably oriented at an angle of approximately 10–20 degrees to minimize the amount of deformation of plate 12 which is required to insert the post devices 14 into holes 40.

Although slanted leg portions 18 are preferred for increased stability, post devices 14 may also extend in a direction substantially perpendicular to the underside of the plate member 12. With the perpendicular post devices 14, upward deformation may not be required to align the tips 40 of the post devices with the holes 24 formed in the bone sections.

In the previously described embodiments of the invention, bone fixation apparatus 10 was particularly suitable for the fixation of bone to bone. FIGS. 9–11 show alternative embodiments of the invention where bone fixation apparatus 10 is employed to affix or anchor soft tissue to bone. Turning to FIG. 9, bone fixation device 50 includes a post device 52 having an enlarged end portion 53 and a leg portion 54 which may be slipped into a hole 55 formed in bone. The leg portion 54 of the post device 52 is of sufficient length to substantially resist forces substantially parallel to the surface of the bone, providing an anchor for securing soft tissue to bone. As with the embodiments of FIGS. 1–8, leg portion 54 is preferably formed so that it slips into hole 55 with minimal force. If desired, the leg portion 54 be shaped to provide a limited area of engagement with the walls of the hole 55 to allow the surgeon to conveniently manipulate the bone fixation apparatus 50 without pulling leg portion 54 from hole 55.

A suturing element 58 having one end coupled to the post device 52 is used to attach the soft tissue, generally designated 56, to the post device 52. The suturing element 58 may be coupled to the post device 52 by tying or wrapping the suturing element around the leg portion below the enlarged end 53. Alternatively, post device 52 may be integrally or monolithically formed with the suturing element 58 as shown in FIG. 10 or the post 52 may be formed with ring 60 to which suturing element 58 may be attached as is shown in FIG. 11. In the modification shown in FIG. 12, post device 52 anchors a surgical plate 62 to the bone and the suturing element 58 is secured to the surgical plate 62. In the modification shown in FIG. 11, the suturing element is passed through aperture 64 and tied to the plate 62. It will be understood that other means in accordance with the invention may also be employed to affix the suturing element to the surgical plate or the post. Although not shown, the post device may be inserted through an aperture formed in the suturing plate or other similar surgical member as a tack. The opposite end of the suturing element may be attached to the soft tissue 56, as shown in FIG. 9. Alternatively, the opposite end of the suturing element may be secured to a second fastening element, with the soft tissue being supported by the loop of the suturing element between the secured ends. The post device and suturing element of the present invention secure the soft tissue to the post device and holding the tissue in the desired position by essentially suspending the tissue from the anchored post device. By adjusting the length of the suturing element and the position of the post device, bone fixation apparatus 50 may be conveniently employed to hold the soft tissue in the desired position during the healing process.

As is apparent from the foregoing description, the bone fixation apparatus of the present invention is particularly suitable for holding bone sections or soft tissue in the desired position. The post devices anchor the surgical member, such as the surgical plate or suturing element, to bone without securely engaging the bone and attaching the surgical member to the bone surface. With the present invention, the size of the post device may be minimized. For example, the post device may have a leg diameter on the order of about 1 mm. The bone fixation apparatus of the present invention may be formed of any suitable bio-compatible or absorbable materials. Examples of suitable materials include, but are not limited to, bio-compatible metals, bio-compatible elastomers exhibiting sufficient stiffness properties and other bio-compatible polymers, and bio-absorbable polymers which are partially or completely absorbed by the body after time may also be used.

What is claimed is:

1. A bone fixation apparatus for anchoring a surgical member to bone, said bone having an outer surface and at least one hole formed therein having an interior diameter and a longitudinal axis, said bone fixation apparatus being adapted to engage said surgical member, said bone fixation apparatus having an elongate leg portion configured for slidable insertion into said hole, said leg portion having a cylindrical wall having an exterior diameter less than said interior diameter of said hole so that said cylindrical wall of said leg portion is substantially discrete from the inner wall of said hole for substantially unrestricted movement of said leg portion into and out of said hole in a direction parallel to said longitudinal axis of said hole, said leg portion being of sufficient length relative to said interior diameter of said hole to resist removal of said leg portion from said hole when forces having an orientation substantially parallel to said outer surface of said bone and at an angle relative to said longitudinal axis of said hole are applied to said post device to thereby anchor said surgical member to said bone, said bone fixation apparatus having an enlarged end portion opposite said leg portion having a maximum width greater than the interior diameter of said hole, said enlarged end having a mating surface configured to engage a portion of said bone around said hole and the longitudinal axis of said leg portion being oriented at an angle of about 15 to 55 degrees relative to said mating surface.

2. A bone fixation apparatus for anchoring a surgical member to bone, said bone having an outer surface and at least one hole formed therein having an interior diameter and a longitudinal axis, said bone fixation apparatus being adapted to engage said surgical member, said bone fixation apparatus having an elongate leg portion configured for slidable insertion into said hole, said leg portion having a cylindrical wall having an exterior diameter less than said interior diameter of said hole so that said cylindrical wall of said leg portion is substantially discrete from the inner wall of said hole for substantially unrestricted movement of said leg portion into and out of said hole in a direction parallel to said longitudinal axis of said hole, said leg portion being of sufficient length relative to said interior diameter of said hole to resist removal of said leg portion from said hole when forces having an orientation substantially parallel to said outer surface of said bone and at an angle relative to said longitudinal axis of said hole are applied to said post device to thereby anchor said surgical member to said bone, said leg portion having a diameter of about 1 mm.

3. A bone fixation apparatus for anchoring a surgical member to bone, said bone having an outer surface and at least one hole formed therein having an interior diameter and a longitudinal axis, said bone fixation apparatus being adapted to engage said surgical member, said bone fixation apparatus having an elongate leg portion configured for slidable insertion into said hole, said leg portion having a cylindrical wall having an exterior diameter less than said interior diameter of said hole so that said cylindrical wall of said leg portion is substantially discrete from the inner wall of said hole for substantially unrestricted movement of said leg portion into and out of said hole in a direction parallel to said longitudinal axis of said hole, said leg portion being of sufficient length relative to said interior diameter of said hole to resist removal of said leg portion from said hole when forces having an orientation substantially parallel to said outer surface of said bone and at an angle relative to said longitudinal axis of said hole are applied to said post device to thereby anchor said surgical member to said bone, and further comprising a ring-shaped end portion opposite said leg portion, said end portion defining an aperture configured for securement of said surgical member to said bone fixation apparatus.

4. In combination, the bone fixation apparatus of claim 3 and a surgical member, said surgical member being an elongated suturing element having a first end extending through said aperture and coupled to said end portion of said bone fixation apparatus and a second end mountable to soft tissue spaced from said hole in said bone.

5. A bone fixation apparatus for anchoring a surgical member to bone, said bone having an outer surface and at least one hole formed therein having an interior diameter and a longitudinal axis, said bone fixation apparatus being adapted to engage said surgical member, said bone fixation apparatus having an elongate leg portion configured for slidable insertion into said hole, said leg portion having a cylindrical wall having an exterior diameter less than said interior diameter of said hole so that said cylindrical wall of said leg portion is substantially discrete from the inner wall of said hole for substantially unrestricted movement of said leg portion into and out of said hole in a direction parallel to said longitudinal axis of said hole, said leg portion being of sufficient length relative to said interior diameter of said hole to resist removal of said leg portion from said hole when forces having an orientation substantially parallel to said outer surface of said bone and at an angle relative to said longitudinal axis of said hole are applied to said post device to thereby anchor said surgical member to said bone, said leg portion having a length of at least about two times said interior diameter of said hole.

6. The bone fixation apparatus of claim 5, and further comprising a surgical member monolithically formed with said bone fixation apparatus.

7. The bone fixation apparatus of claim 5 in which said leg portion has an enlarged portion projecting outwardly from said cylindrical wall, said enlarged portion having a maximum diameter at least as large as said interior diameter of said hole to define a limited contact area where said enlarged portion forms a tight fit with the inner wall of said hole to increase the force required to remove said leg portion from said hole without preventing said leg portion from being pulled in a direction parallel to the longitudinal axis of said hole.

8. The bone fixation apparatus of claim 5, and further comprising an enlarged end portion opposite said leg portion having a maximum width greater than said interior diameter of said hole.

9. The bone fixation apparatus of claim 6 in which said surgical member is a plate configured to extend across a portion of each of said bone sections.

10. The bone fixation apparatus of claim 6 in which said surgical member is an elongated suturing element having one end configured to engage a portion of soft tissue and anchor said soft tissue to said bone.

11. A bone fixation apparatus for anchoring a surgical member to bone, said bone having an outer surface and at least one hole formed therein having an interior diameter and a longitudinal axis, said bone fixation apparatus being adapted to engage said surgical member, said bone fixation apparatus having an elongate leg portion configured for slidable insertion into said hole, said leg portion having a cylindrical wall having an exterior diameter less than said interior diameter of said hole so that said cylindrical wall of said leg portion is substantially discrete from the inner wall of said hole for substantially unrestricted movement of said leg portion into and out of said hole in a direction parallel to said longitudinal axis of said hole, said leg portion being of sufficient length relative to said interior diameter of said hole to resist removal of said leg portion from said hole when forces having an orientation substantially parallel to said outer surface of said bone and at an angle relative to said longitudinal axis of said hole are applied to said post device to thereby anchor said surgical member to said bone, said post device being formed of an absorbable material.

12. A bone fixation apparatus for retaining adjacent bone sections in a desired position during the healing process, said bone sections each having an outer surface and at least one hole formed therein, said hole having an interior diameter, said bone fixation apparatus comprising:

a plate member configured to extend across a portion of each of said bone sections, said plate member having an upper surface and a lower surface positionable on said outer surface of said bone sections, at least one post device carried by said plate member for each of said bone sections, each said post device having a leg portion configured for slidable insertion into said hole, said leg portion having a cylindrical wall having an exterior diameter less than said interior diameter of said hole so that said cylindrical wall of said leg portion is substantially discrete from the inner wall of said hole for substantially unrestricted movement of said leg portion into and out of said hole in a direction parallel to said longitudinal axis of said hole, said leg portion being of sufficient length relative to said interior diameter of said hole to resist removal of said leg portion from said hole when forces having an orientation substantially parallel to said outer surface of said bone sections and at an angle relative to said longitudinal axis of said hole are applied to said post device to thereby anchor said plate member to said bone sections and retain said bone sections in said desired position, said leg portion of said post device being inclined at an angle of about 15 to 55 degrees relative to said lower surface of said plate member.

13. The bone fixation apparatus of claim 12 in which said plate member is resiliently deformable between a first position with said leg portion of each said post device positioned for insertion of said leg portion into said hole and a second position with said leg portion positioned to bias said bone sections together when said leg portion is positioned in said hole.

14. In combination, the bone fixation apparatus of claim 13 and an instrument engaging said plate member and retaining said plate member in said first position.

15. A bone fixation apparatus for retaining adjacent bone sections in a desired position during the healing process, said bone sections each having an outer surface and at least one hole formed therein, said hole having an interior diameter, said bone fixation apparatus comprising:

a plate member configured to extend across a portion of each of said bone sections, said plate member having an upper surface and a lower surface positionable on said outer surface of said bone sections, at least one post device carried by said plate member for each of said bone sections, each said post device having a leg portion configured for slidable insertion into said hole, said leg portion having a cylindrical wall having an exterior diameter less than said interior diameter of said hole so that said cylindrical wall of said leg portion is substantially discrete from the inner wall of said hole for substantially unrestricted movement of said leg portion into and out of said hole in a direction parallel to said longitudinal axis of said hole, said leg portion being of sufficient length relative to said interior diameter of said hole to resist removal of said leg portion from said hole when forces having an orientation substantially parallel to said outer surface of said bone sections and at an angle relative to said longitudinal axis of said hole are applied to said post device to thereby anchor said plate member to said bone sections and retain said bone sections in said desired position, said plate member including a downward depending flange formed on said lower surface thereof, said flange being insertable in a groove formed in at least two adjacent bone sections to resist lateral slippage of said adjacent bone sections.

16. A bone fixation apparatus for retaining adjacent bone sections in a desired position during the healing process, said bone sections each having an outer surface and at least one hole formed therein, said hole having an interior diameter, said bone fixation apparatus comprising:

a plate member configured to extend across a portion of each of said bone sections, said plate member having an upper surface and a lower surface positionable on said outer surface of said bone sections, at least one post device carried by said plate member for each of said bone sections, each said post device having a leg portion configured for slidable insertion into said hole, said leg portion having a cylindrical wall having an exterior diameter less than said interior diameter of said hole so that said cylindrical wall of said leg portion is substantially discrete from the inner wall of said hole for substantially unrestricted movement of said leg portion into and out of said hole in a direction parallel to said longitudinal axis of said hole, said leg portion being of sufficient length relative to said interior diameter of said hole to resist removal of said leg portion from said hole when forces having an orientation substantially parallel to said outer surface of said bone sections and at an angle relative to said longitudinal axis of said hole are applied to said post device to thereby anchor said plate member to said bone sections and retain said bone sections in said desired position, and a fastener mountable to said plate member and one of said bone sections to secure said plate member to said one of said bone sections, said fastener having a longitudinal axis, said fastener being configured to substantially resist removal of said fastener from said bone upon application of a force substantially parallel to said longitudinal axis.

17. A bone fixation apparatus for retaining adjacent bone sections in a desired position during the healing process, said bone sections each having an outer surface and at least one hole formed therein, said hole having an interior diameter, said bone fixation apparatus comprising:

a plate member configured to extend across a portion of each of said bone sections, said plate member having an upper surface and a lower surface positionable on said outer surface of said bone sections, at least one post device carried by said plate member for each of said bone sections, each said post device having a leg portion configured for slidable insertion into said hole, said leg portion having a cylindrical wall having an exterior diameter less than said interior diameter of said hole so that said cylindrical wall of said leg portion is substantially discrete from the inner wall of said hole for substantially unrestricted movement of said leg portion into and out of said hole in a direction parallel to said longitudinal axis of said hole, said leg portion being of sufficient length relative to said interior diameter of said hole to resist removal of said leg portion from said hole when forces having an orientation substantially parallel to said outer surface of said bone sections and at an angle relative to said longitudinal axis of said hole are applied to said post device to thereby anchor said plate member to said bone sections and retain said bone sections in said desired position, said plate member being formed of a section of arbitrary shape of a continuous, elongated sheet of surgical plate material.

18. A bone fixation apparatus for retaining adjacent bone sections in a desired position during the healing process, said bone sections each having an outer surface and at least one hole formed therein, said hole having an interior diameter, said bone fixation apparatus comprising:

a plate member configured to extend across a portion of each of said bone sections, said plate member having an upper surface and a lower surface positionable on said outer surface of said bone sections, at least one post device carried by said plate member for each of said bone sections, each said post device having a leg portion configured for slidable insertion into said hole, said leg portion having a cylindrical wall having an exterior diameter less than said interior diameter of said hole so that said cylindrical wall of said leg portion is substantially discrete from the inner wall of said hole for substantially unrestricted movement of said leg portion into and out of said hole in a direction parallel to said longitudinal axis of said hole, said leg portion being of sufficient length relative to said interior diameter of said hole to resist removal of said leg portion from said hole when forces having an orientation substantially parallel to said outer surface of said bone sections and at an angle relative to said longitudinal axis of said hole are applied to said post device to thereby anchor said plate member to said bone sections and retain said bone sections in said desired position, at least one of said plate member and said post device are formed of an absorbable material.

19. The bone fixation apparatus of claim 18 in which said leg portion has an enlarged portion projecting outwardly from said cylindrical wall, said enlarged portion having a maximum diameter at least as large as said interior diameter of said hole to define a limited contact area where said enlarged portion is in tight fitting engagement with the inner wall of said bole to increase the force required to remove said leg portion from said hole without preventing said leg portion from being pulled in a direction parallel to the longitudinal axis of said hole.

20. The bone fixation apparatus of claim 18 in which said post device is monolithically formed with said plate member.

21. The bone fixation apparatus of claim 18 in which said plate member has a plurality of apertures formed therein, each said post device being positioned in one of said apertures with said leg portion of said post device depending from said lower surface of said plate member.

22. The bone fixation apparatus of claim 18 in which plate member is anchored to one of said bone sections by at least two of said post devices.

23. The bone fixation apparatus of claim 21 in which said post device includes an enlarged end portion shaped to engage a portion of said upper surface of said plate member adjacent said one of said apertures.

24. A method of retaining adjacent bone sections in a desired position during the healing process comprising the steps of:

providing a bone fixation apparatus having a plate member configured to extend across a portion of each of said bone sections and a plurality of said post devices carried by said plate member, each of said post devices having an elongate leg portion with a cylindrical surface having an outer diameter, forming at least one hole in each of said bone sections, said hole having an inner diameter, slipping said leg portion of each of said post devices into one of said holes to mount said plate member to said bone sections, said leg portion being slidable within said hole in a direction parallel to the longitudinal axis of said hole for substantially unrestrained movement of said leg portion into and out of said hole, said leg portion having a length relative to said inner diameter of said hole to resist removal of said leg portion from said hole when forces having an orientation substantially parallel to the outer surface of said bone sections and at an angle relative to the longitudinal axis of said hole are applied to said post devices so that said post devices anchor said plate member to said bone sections and retain said bone sections in said desired position during said healing process.

25. The method of claim 24 in which said providing step includes providing a resilient plate member, and further comprising the step of resiliently deforming said plate member to substantially align the tips of each of said leg portions with one of said holes.

26. The method of claim 24 in which said providing step includes providing a post device having an enlarged portion projecting from said cylindrical surface, said enlarged portion defining a maximum diameter of said leg portion, and in which said forming step includes forming said hole with an inner diameter no greater than said maximum diameter so that said enlarged portion defines a limited contact area where said leg portion forms a tight fit with the inner wall of said hole to partially restrain sliding movement of said leg portion within said hole during manual manipulation of said plate member relative to said bone sections.

27. The method of claim 24 in which said providing step includes providing a continuous, elongated sheet of surgical plate material, and further comprising the steps of determining the configuration of said adjacent bone sections and cutting a plate member from said elongated sheet of surgical plate material having a desired shape for covering said portion of each of said bone sections.

* * * * *